(12) United States Patent
Hasegawa et al.

(10) Patent No.: US 10,259,772 B2
(45) Date of Patent: Apr. 16, 2019

(54) AGENTS FOR MAINTAINING UNDIFFERENTIATED STATE AND PROMOTING PROLIFERATION OF STEM CELLS

(71) Applicant: NIPPON MENARD COSMETIC CO., LTD., Nagoya-shi, Aichi (JP)

(72) Inventors: Seiji Hasegawa, Nagoya (JP); Yu Inoue, Nagoya (JP); Yuichi Hasebe, Nagoya (JP); Tsutomu Sakaida, Nagoya (JP)

(73) Assignee: Nippon Menard Cosmetic Co., Ltd., Nagoya-shi, Aichi (JP)

( * ) Notice: Subject to any disclaimer, the term of this patent is extended or adjusted under 35 U.S.C. 154(b) by 0 days.

(21) Appl. No.: 15/524,752

(22) PCT Filed: Nov. 5, 2015

(86) PCT No.: PCT/JP2015/081109
§ 371 (c)(1),
(2) Date: May 5, 2017

(87) PCT Pub. No.: WO2016/072435
PCT Pub. Date: May 12, 2016

(65) Prior Publication Data
US 2017/0320809 A1 Nov. 9, 2017

(30) Foreign Application Priority Data

Nov. 6, 2014 (JP) .................................. 2014-226389

(51) Int. Cl.
| | | |
|---|---|---|
| *A61K 31/231* | (2006.01) | |
| *A61K 31/225* | (2006.01) | |
| *A61K 9/107* | (2006.01) | |
| *C07C 69/602* | (2006.01) | |
| *A61K 8/37* | (2006.01) | |
| *A61Q 19/00* | (2006.01) | |
| *A61K 35/12* | (2015.01) | |
| *A23L 33/12* | (2016.01) | |
| *A23L 2/52* | (2006.01) | |
| *A61K 8/02* | (2006.01) | |
| *A61K 8/04* | (2006.01) | |
| *A61K 8/06* | (2006.01) | |
| *A61K 9/00* | (2006.01) | |
| *A61K 9/06* | (2006.01) | |
| *A61K 9/20* | (2006.01) | |
| *A61K 31/232* | (2006.01) | |

(Continued)

(52) U.S. Cl.
CPC .............. *C07C 69/602* (2013.01); *A23L 2/52* (2013.01); *A23L 33/12* (2016.08); *A61K 8/0216* (2013.01); *A61K 8/042* (2013.01); *A61K 8/06* (2013.01); *A61K 8/37* (2013.01); *A61K 8/375* (2013.01); *A61K 9/0095* (2013.01); *A61K 9/06* (2013.01); *A61K 9/107* (2013.01); *A61K 9/20* (2013.01); *A61K 31/231* (2013.01); *A61K 31/232* (2013.01); *A61K 35/12* (2013.01); *A61P 17/02* (2018.01); *A61Q 19/00* (2013.01); *C07C 69/52* (2013.01); *C07C 69/587* (2013.01); *C12N 5/0606* (2013.01); *A23V 2002/00* (2013.01); *A61K 2800/74* (2013.01); *C12N 15/09* (2013.01); *C12N 2501/999* (2013.01)

(58) Field of Classification Search
CPC ..... A61K 31/231; A61K 31/225; A61K 9/107
See application file for complete search history.

(56) References Cited

U.S. PATENT DOCUMENTS 5,077,312 A * 12/1991 Shoyab .................. A61K 31/23
514/547
2006/0127373 A1  6/2006 Son et al.
(Continued)

FOREIGN PATENT DOCUMENTS

EP    1 452 175 A1    9/2004
EP    1 897 530 A1    3/2008
(Continued)

OTHER PUBLICATIONS

Das et al. Cancer Metastasis Rev., 2011, vol. 30, pp. 311-324.*
(Continued)

*Primary Examiner* — Samira J Jean-Louis
(74) *Attorney, Agent, or Firm* — Birch, Stewart, Kolasch & Birch, LLP

(57) ABSTRACT

An object of the present invention is to find a novel substance that is capable of efficiently promoting the proliferation of stem cells while maintaining the undifferentiated state thereof and to provide the substance as an agent for maintaining the undifferentiated state of stem cells or an agent for promoting the proliferation of stem cells. Another object of the present invention is to provide an agent for treating a wound that has a wound healing effect on the skin and is readily available in the field of skin regenerative medicine or cosmetic treatment, and safe and inexpensive. The present invention relates to an agent for maintaining the undifferentiated state or promoting the proliferation of stem cells or an agent for treating a wound, comprising, as an active ingredient, one or a mixture of two or more of fatty acid glycerides represented by the following general formula (I):

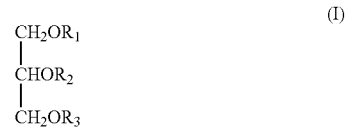

wherein at least one of $R_1$, $R_2$, and $R_3$ represents an acyl group derived from an unsaturated fatty acid having 16 to 22 carbon atoms and the others each represent an acyl group derived from a saturated fatty acid or a hydrogen atom.

8 Claims, No Drawings
Specification includes a Sequence Listing.

(51) Int. Cl.
| | |
|---|---|
| C07C 69/52 | (2006.01) |
| C07C 69/587 | (2006.01) |
| C12N 5/0735 | (2010.01) |
| A61P 17/02 | (2006.01) |
| C12N 15/09 | (2006.01) |

(56) References Cited

U.S. PATENT DOCUMENTS

2007/0142306 A1  6/2007  Maurel et al.
2008/0200543 A1  8/2008  Kim

FOREIGN PATENT DOCUMENTS

| EP | 3 153 163 A1 | 4/2017 |
|---|---|---|
| JP | 6-503085 A | 4/1994 |
| JP | 7-17844 A | 1/1995 |
| JP | 2002-525042 A | 8/2002 |
| JP | 2002-532531 A | 10/2002 |
| JP | 2004-24089 A | 1/2004 |
| JP | 3573354 B2 | 10/2004 |
| JP | 2005-47904 A | 2/2005 |
| JP | 2006-124389 A | 5/2006 |
| JP | 2006-342074 A | 12/2006 |
| JP | 2010-502662 A | 1/2010 |
| JP | 2010-120860 A | 6/2010 |
| RU | 2150936 C1 | 6/2000 |
| RU | 2 341 257 C2 | 12/2008 |
| RU | 2012 120 713 A | 11/2013 |
| WO | WO 92/10995 A1 | 7/1992 |
| WO | WO 99/26640 A1 | 6/1999 |
| WO | WO 00/15764 A2 | 3/2000 |
| WO | WO 00/37040 A1 | 6/2000 |
| WO | WO 01/85158 A3 | 11/2001 |
| WO | WO 2008/028631 A2 | 3/2008 |
| WO | WO 2008/143928 A1 | 11/2008 |
| WO | WO 2009/081611 A1 | 7/2009 |
| WO | WO 2009/147400 A1 | 12/2009 |
| WO | WO 2010/006261 A1 | 1/2010 |
| WO | WO 2011/048350 A1 | 4/2011 |
| WO | WO 2011/064524 A1 | 6/2011 |

OTHER PUBLICATIONS

Zhang et al. Cell Stem Cell, 2012, vol. 11, pp. 589-595.*
Champion et al., Textbook of Dermatology, 1998, vol. 1, pp. 342-343.
Goodell et al., "Dye efflux studies suggest that hematopoietic stem cells expressing low or undetectable levels of CD34 antigen exist in multiple species", Nature Meddicine, Dec. 1997, vol. 3, No. 12, pp. 1337-1345.
Hasegawa, "Application of stem cell research in the field of cosmetic dermatology", Aesthetic Dermatology, 2013, vol. 23, pp. 1-11.
International Preliminary Report on patentability for PCT/JP2015/081109 (PCT/IPEA/409) dated Aug. 24, 2016.
International Search Report or PCT/JP2015/081109 dated Feb. 9, 2016.
Kitagawa et al., "A challenge to the implementation of the industrialization of regenerative medicine", Regenerative Medicine (The Japanese Society for Regenerative Medicine), 2008, vol. 7, No. 1, pp. 14-18.
Mabuchi et al., "Prospective isolation and identification of mesenchymal stem cells", Regenerative Medicine (The Japanese Society for Regenerative Medicine), 2007, vol. 6, No. 3, pp. 263-268.
Madlambayan et al., Abstract of "Controlling culture dynamics for the expansion of hematopoietic stem cells", J. Hematother Stem Cell Res, Aug. 2001, vol. 10, No. 4, pp. 481-492, total 2 pages.
Pittenger et al., "Multilineage Potential of Adult Human Mesenchymal Stem Cells", Science, Apr. 2, 1999, vol. 284, pp. 143-147, total 6 pages.
Reubinoff et al., "Embryonic stem cell lines from human blastocysts: somatic differentiation in vitro", Nature Biotechnology, Apr. 2000, vol. 18, pp. 399-404.
28 29 Smith et al., "Buffalo Rat Liver Cells Produce a Diffusible Activity Which Inhibits the Differentiation of Murine Embryonal Carcinoma and Embryonic Stem Cells", Developmental Biology, 1987, vol. 121, pp. 1-9.
Suzuki et al., "Flow-Cytometric Separation and Enrichment of Hepatic Progenitor Cells in the Developing Mouse Liver", Hepatology, 2000, vol. 32, No. 6, pp. 1230-1239.
Thomson et al., "Embryonic Stem Cell Lines Derived from Human Blastocysts", Science, Nov. 6, 1998, vol. 282, pp. 1145-1147, total 4 pages.
Thomson et al., "Isolation of a primate embryonic stem cell line", Proc. Natl. Acad. Sci. USA, Aug. 1995, vol. 92, pp. 7844-7848.
Van Der Laan et al., "Infection by porcine endogenous retrovirus after islet xenotransplantation in SCID mice", Nature, Sep. 2000, vol. 407, pp. 90-94.
Written Opinion of the International Searching Authority for PCT/JP2015/081109 (PCT/ISA/237) dated Feb. 9, 2016.
Zuk et al., "Multilineage Cells from Human Adipose Tissue: Implications for Cell-Based Therapies", Tissue Engineering, 2001, vol. 7, No. 2, pp. 211-228.
Zulewski et al., "Multipotential Nestin-Positive Stem Cells Isolated From Adult Pancreatic Islets Differentiate Ex Vivo Into Pancreatic Endocrine, Exocrine, and Hepatic Phenotypes", Diabetes, Mar. 2001, vol. 50, pp. 521-533.
Russian Office Action with English Translation dated Apr. 2, 2018 for corresponding Russian Application No. 2017118433.
Ferreira et al., "The Use of Fatty Acids in Wound Care: An Integrative Review of the Brazilian Literature", Rev Esc Enferm USP, 2012; 46(3), pp. 745-753, with abstract.
Korean Office Action dated Aug. 6, 2018 for Korean Application No. 10-2017-7013020.
Russian Office Action with English Translation dated Aug. 8, 2018 for corresponding Russian Application No. 2017118433.
Database WPI, Week 200550, Thomson Scientific, London, GB; AN 2005-497549, XP002781480, Jun. 30, 2005.
Exended European Search Report for corresponding EP Application No. 15856813.9 dated Jun. 8, 2018.
Pellicier et al., "A Model for Human Adipocytes in 3D Culture", Obesity Facts, May 2012, vol. 5, p. 156.
Database WPI Week 201357 Thomson Scientific, London, GB; AN 2013-L14166, XP & KR 2013 0058299A, Jun. 4, 2013.
European Patent Office Action dated Feb. 11, 2019 for European Patent Application No. 15856813.9.

* cited by examiner

SEQUENCE LISTING

```
<160> NUMBER OF SEQ ID NOS: 4

<210> SEQ ID NO 1
<211> LENGTH: 20
<212> TYPE: DNA
<213> ORGANISM: Artificial
<220> FEATURE:
<223> OTHER INFORMATION: primer

<400> SEQUENCE: 1
atgcctgcag tttttcatcc                                          20

<210> SEQ ID NO 2
<211> LENGTH: 20
<212> TYPE: DNA
<213> ORGANISM: Artificial
<220> FEATURE:
<223> OTHER INFORMATION: primer

<400> SEQUENCE: 2
gaggcaggtc ttcagaggaa                                          20
```

```
<210> SEQ ID NO 3
<211> LENGTH: 20
<212> TYPE: DNA
<213> ORGANISM: Artificial
<220> FEATURE:
<223> OTHER INFORMATION: primer

<400> SEQUENCE: 3
tgcaccacca actgcttagc                                                     20

<210> SEQ ID NO 4
<211> LENGTH: 20
<212> TYPE: DNA
<213> ORGANISM: Artificial
<220> FEATURE:
<223> OTHER INFORMATION: primer

<400> SEQUENCE: 4
tcttctgggt ggcagtgatg                                                     20
```

AGENTS FOR MAINTAINING UNDIFFERENTIATED STATE AND PROMOTING PROLIFERATION OF STEM CELLS

TECHNICAL FIELD

The present invention relates to an agent for maintaining the undifferentiated state or promoting the proliferation of stem cells or for treating a wound and a method for promoting the proliferation of stem cells and a method for maintaining the undifferentiated state of stem cells.

BACKGROUND ART

Tissue in vertebrates (in particular mammals) responds to cell or organ damage associated with an injury or a disease or aging by activating the regenerating system to recover from the cell or organ damage. Stem cells (tissue stem cells, somatic stem cells) that reside in the tissue play a significant role in this response. Stem cells have multipotency to differentiate into any cell or organ and are considered to compensate the cell or organ damage with this property to achieve the recovery. The regenerative medicine, the next-generation medicine that employs such stem cells, has raised high expectations.

The tissue for which stem cell studies are most advanced in mammal is bone marrow. It has been revealed that bone marrow contains hematopoietic stem cells of the living body and is the source of reproduction of all hemocytes. Furthermore, it has been reported that bone marrow contains stem cells that can differentiate into organs and tissues (e.g., bone, cartilage, muscle, fat, and the like), besides hematopoietic stem cells (see Non-Patent Document 1).

Recently, it has been further revealed that stem cells reside in every organ and tissue, such as skin, liver, pancreas, and fat, besides bone marrow and are responsible for the reproduction of each organ or tissue and maintenance of homeostasis (see Non-Patent Document 2 to 5). Moreover, stem cells that reside in organs and tissues have excellent plasticity and may be available in the reproduction of an organ or tissue whose self-replication has been impossible so far.

On the other hand, some of these stem cells have been known to decrease with aging and techniques for preventing the decrease of stem cells for maintaining homeostasis of the tissues have been actively studied (Non-Patent Document 6). Recently, techniques for culturing stem cells after the separation from living tissue for the proliferation thereof have been also developed in the fields of cell transplantation therapy and tissue engineering (regenerative medicine and regenerative cosmetic treatment) to apply the ability (multipotency) of stem cells to the reproduction of an organ or tissue (Non-Patent Documents 7 and 8).

In particular, it is very important for culturing stem cells in vitro to proliferate the stem cells while maintaining a state in which multipotency, the ability of stem cells, is maintained, that is, an undifferentiated state. The induction of differentiation by failing to maintain the undifferentiated state of the stem cells during the culture will result in the loss of the ability (multipotency) of the stem cells finally prepared and the failure to achieve the effect of interest (reproduction of an organ or tissue, or the like).

Based on the foregoing, it must be possible to culture stem cells while maintaining the undifferentiated state in order to use stem cells in cell transplantation therapy and tissue engineering (regenerative medicine and regenerative cosmetic treatment) for reproduction of an organ or tissue.

To date, some techniques for proliferating stem cells while maintaining the undifferentiated state have been reported, but such techniques are yet developing. For example, embryonic stem cells (ES cells) and hematopoietic stem cells can be maintained in an undifferentiated state by coculturing them with sustaining cells (stromal or feeder cells) (see Patent Document 1 and Non-Patent Documents 9 to 11). However, cases of infection with endogenous virus derived from feeder cells transmitted between different species of animals have been reported recently (cf. Non-Patent Document 12) and culturing stem cells using sustaining cells is not suitable for the culture of stem cells for medical applications.

Other methods include a method for maintaining the undifferentiated state of stem cells by combining cytokines complicatedly. For example, murine ES cells can be maintained in an undifferentiated state by adding LIF (Leukemia Inhibitory Factor)) to the medium (see Patent Document 2 and Non-Patent Document 13). In addition, the undifferentiated state has been reported to be maintained in the presence of early acting cytokines thrombopoietin (TPO), interleukin-6 (IL-6), FLT-3 ligand, and Stem Cell Factor (SCF) in embryonic stem cells, somatic stem cells, and the like (see Patent Document 3 and Non-Patent Document 14).

However, cytokines are expensive, problematic in harvesting their sources and storing, and difficult to be used in an easy way. In addition, it has been revealed that the effect of LIF is limited to very specific cell lines and ES cells and somatic stem cells in primate, in particular, cannot be maintained in an undifferentiated state only by the addition of LIF (see Non-Patent Document 10).

As seen above, currently reported methods for maintaining the undifferentiated state of stem cells require complicated manipulation and are not effective in maintaining the undifferentiated state. Therefore, a technique for proliferating stem cells while maintaining the undifferentiated state has been desired to use stem cells for regenerative medicine. Accordingly, a technique for proliferating stem cells safely, easily, and effectively while maintaining the undifferentiated state been desired.

Recently, patients with chronic wound such as diabetic foot ulcer or decubitus ulcer, which are hard to be treated only by epidermization have been increasing with increase of diabetes and arteriosclerosis and aging. Usually, a wound in the skin is treated with first aid such as washing of the wound and allowed to cure spontaneously by the healing ability of the living body. However, a wound healing is sometimes required to be promoted since natural healing may take a long time depending on the severity of the wound and elderly people and diabetic patients are in particular slow in natural healing in comparison with young people. As agents for promoting a wound healing in the skin, lysozyme chloride, solcoseryl, and the like are known but any of them has been hardly sufficiently effective in promoting a wound healing. In the wound healing of skin, tissue is reconstructed and therefore the migration of required cells and the production of extracellular matrices such as collagen are promoted. Type 3 collagen, which is mainly produced early in wound healing and is important for the reconstruction of tissue, has a promoting effect on wound healing and is used as an agent for promoting a wound healing (Non-Patent Document 15 and Patent Document 4). Moreover, as materials that stimulate the proliferation or differentiation of stem cells and promote a wound healing, substance P (Patent Document 5) and the like are known. However, these substances are problematic in cost and storage stability because of being protein and not suited for the case where a large amount of skin regenerative treatment in a short period of time, such as therapy application is required. Moreover, increased awareness of cosmetic treatment and anti-aging has heightened interest in regenerative cosmetic treatments of skin for improvement of wrinkles, slackness and pigmentation caused by aging and ultraviolet rays. Therefore, a substance that can be obtained easily, safe, and inexpensive is desired for skin regenerative medicine such as wound healing or regenerative cosmetic treatment of skin.

PRIOR ART DOCUMENTS

Patent Documents

[Patent Document 1] JP Patent Publication (Kokai) No. 2004-24089 A
[Patent Document 2] JP Patent Publication (Kohyo) No. 2002-525042 A
[Patent Document 3] JP Patent No. 3573354
[Patent Document 4] JP Patent Publication (Kokai) No. 7-17844 A (1995)
[Patent Document 5] JP Patent Publication (Kokai) No. 2006-124389 A Non-Patent Documents

[Non-Patent Document 1] Pittenger M. F., et al., Science, 1999, Vol. 284, pp. 143-147
[Non-Patent Document 2] Goodell M. A., et al., Nat. Med., 1997, Vol. 3, pp. 1337-1345
[Non-Patent Document 3] Zulewski H., et al., Diabetes, 2001, Vol. 50, pp. 521-533
[Non-Patent Document 4] Suzuki A., et al., Hepatology, 2000, Vol. 32, pp. 1230-1239
[Non-Patent Document 5] Zuk P. A., et al., Tissue Engineering, 2001, Vol. 7, pp. 211-228
[Non-Patent Document 6] HASEGAWA Seiji, et al., Aesthetic Dermatology, 2013, Vol. 23, pp. 1-11
[Non-Patent Document 7] MABUCHI Yo, et al., Regenerative Medicine (The Japanese Society for Regenerative Medicine), 2007, Vol. 6, pp. 263-268
[Non-Patent Document 8] KITAGAWA Akira, et al., Regenerative Medicine (The Japanese Society for Regenerative Medicine), 2008, Vol. 7, pp. 14-18
[Non-Patent Document 9] Thomson J. A., et al., Proc. Natl. Acad. Sci. USA, 1995, Vol. 92, pp. 7844-7848
[Non-Patent Document 10] Thomson J. A., et al., Science, 1998, Vol. 282, pp. 1145-1147
[Non-Patent Document 11] Reubinoff B. E., et al., Nature Biotech., 2000, Vol. 18, pp. 399-404
[Non-Patent Document 12] van der Laan L. J., et al., Nature, 2000, Vol. 407, pp. 90-94
[Non-Patent Document 13] Smith A. G., et al., Dev. Biol., 1987, Vol. 121, pp. 1-9
[Non-Patent Document 14] Madlambayan G. J., et al., J. Hemather. Stem Cell Res., 2001, Vol. 10, pp. 481-492
[Non-Patent Document 15] R. H. CHAMPION et al, Textbook of Dermatology, vol. 1.1: 342-343, 1998

SUMMARY OF INVENTION

Problems to be Solved by the Invention

In view of the circumstances described above, an object of the present invention is to find a novel substance that is capable of efficiently promoting the proliferation of stem cells while maintaining the undifferentiated state thereof and to provide the substance as an agent for maintaining the undifferentiated state of stem cells or an agent for promoting the proliferation of stem cells. Another object of the present invention is to provide an agent for treating a wound that has a wound healing effect on the skin and is readily available in the field of skin regenerative medicine or regenerative cosmetic treatment, and safe and inexpensive.

Means for Solving the Problem

The present inventors have studied diligently to achieve the aforementioned objects and found, as a result, that fatty acid glycerides having an acyl group derived from an unsaturated fatty acid having a certain number of carbon atoms, wherein the fatty acid glycerides are main ingredients of plant and animal oils and fats, and the like and widely used as emulsifiers and edible oils in cosmetics and foods, have excellent undifferentiated state-maintaining effect, proliferation promoting effect, and wound healing effect on stem cells that have not known till now, thereby completing the present invention.

Accordingly, the present invention encompasses the following.

(1) An agent for maintaining the undifferentiated state of stem cells, comprising, as an active ingredient, one or a mixture of two or more of fatty acid glycerides represented by the following general formula (I):

[Formula 1]

wherein at least one of $R_1$, $R_2$, and $R_3$ represents an acyl group derived from an unsaturated fatty acid having 16 to 22 carbon atoms and the others each represent an acyl group derived from a saturated fatty acid or a hydrogen atom.

(2) An agent for promoting the proliferation of stem cells, comprising, as an active ingredient, one or a mixture of two or more of fatty acid glycerides represented by the following general formula (I):

[Formula 2]

wherein at least one of $R_1$, $R_2$, and $R_3$ represents an acyl group derived from an unsaturated fatty acid having 16 to 22 carbon atoms and the others each represent an acyl group derived from a saturated fatty acid or a hydrogen atom.

(3) An agent for treating a wound, comprising, as an active ingredient, one or a mixture of two or more of fatty acid glycerides represented by the following general formula (I):

[Formula 3]

(I)

wherein at least one of $R_1$, $R_2$, and $R_3$ represents an acyl group derived from an unsaturated fatty acid having 16 to 22 carbon atoms and the others each represent an acyl group derived from a saturated fatty acid or a hydrogen atom.

(4) The agent according to any of (1) to (3), wherein the unsaturated fatty acid is selected from the group consisting of docosahexaenoic acid, eicosapentaenoic acid, arachidonic acid, α-linolenic acid, γ-linolenic acid, linoleic acid, and oleic acid.

(5) A cosmetic product comprising the agent according to any of (1) to (3).

(6) A pharmaceutical product or quasi drug comprising the agent according to any of (1) to (3).

(7) A food or drink comprising the agent according to any of (1) to (3).

(8) A method for producing stem cells, comprising culturing stem cells in a medium comprising one or a mixture of two or more of fatty acid glycerides represented by the following general formula (I):

[Formula 4]

(I)

wherein at least one of $R_1$, $R_2$, and $R_3$ represents an acyl group derived from an unsaturated fatty acid having 16 to 22 carbon atoms and the others each represent an acyl group derived from a saturated fatty acid or a hydrogen atom.

(9) A method for maintaining the undifferentiated state of stem cells, comprising culturing stem cells in a medium comprising one or a mixture of two or more of fatty acid glycerides represented by the following general formula (I):

[Formula 5]

(I)

wherein at least one of $R_1$, $R_2$, and $R_3$ represents an acyl group derived from an unsaturated fatty acid having 16 to 22 carbon atoms and the others each represent an acyl group derived from a saturated fatty acid or a hydrogen atom.

(10) A method for promoting the proliferation of stem cells, comprising culturing stem cells in a medium comprising one or a mixture of two or more of fatty acid glycerides represented by the following general formula (I):

[Formula 6]

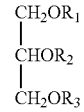

(I)

wherein at least one of $R_1$, $R_2$, and $R_3$ represents an acyl group derived from an unsaturated fatty acid having 16 to 22 carbon atoms and the others each represent an acyl group derived from a saturated fatty acid or a hydrogen atom.

(11) The method according to any of (8) to (10), wherein the unsaturated fatty acid is selected from the group consisting of docosahexaenoic acid, eicosapentaenoic acid, arachidonic acid, α-linolenic acid, γ-linolenic acid, linoleic acid, and oleic acid.

(12) A method for treating a wound in a mammal, comprising administering an effective amount of the agent for treating a wound according to (3) to the mammal.

(13) A fatty acid glyceride for use in treating a wound, wherein the fatty acid glyceride is represented by the following general formula (I):

[Formula 7]

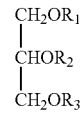

(I)

wherein at least one of $R_1$, $R_2$, and $R_3$ represents an acyl group derived from an unsaturated fatty acid having 16 to 22 carbon atoms and the others each represent an acyl group derived from a saturated fatty acid or a hydrogen atom.

(14) Use of a fatty acid glyceride for producing an agent for treating a wound, wherein the fatty acid glyceride is represented by the following general formula (I):

[Formula 8]

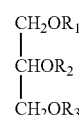

(I)

wherein at least one of R1, R2, and R3 represents an acyl group derived from an unsaturated fatty acid having 16 to 22 carbon atoms and the others each represent an acyl group derived from a saturated fatty acid or a hydrogen atom.

This patent application claims priority from Japanese Patent Application No. 2014-226389 filed on Nov. 6, 2014, and the disclosure of which is hereby incorporated by reference.

Effects of the Invention

According to the present invention, stem cells can be efficiently proliferated while maintaining the undifferentiated state. According to the present invention, a wound can be also healed effectively. Therefore, the present invention can contribute greatly to the field of regenerative medicine and regenerative cosmetic treatment.

EMBODIMENTS FOR CARRYING OUT THE INVENTION

The present invention will be described in detail below.

An agent for maintaining the undifferentiated state or promoting the proliferation of stem cells or an agent for treating a wound according to the present invention comprises fatty acid glyceride represented by the following general formula (I) having an acyl group derived from an unsaturated fatty acid having a certain number of carbon atoms (hereinafter, simply referred to as "fatty acid glycerides").

[Formula 9]

$$\begin{array}{c} CH_2OR_1 \\ | \\ CHOR_2 \\ | \\ CH_2OR_3 \end{array} \quad (I)$$

wherein at least one of $R_1$, $R_2$, and $R_3$ represents an acyl group derived from an unsaturated fatty acid having 16 to 22 carbon atoms and the others each represent an acyl group derived from a saturated fatty acid or a hydrogen atom.

Unsaturated fatty acids having 16 to 22 carbon atoms from which the aforementioned acyl group is derived are naturally widely distributed fatty acids having 1 to 6 double bonds and specific examples include such as palmitoleic acid (9-hexadecenoic acid), oleic acid (cis-9-octadecenoic acid), linoleic acid (9Z,12Z-octadecadiene acid), vaccenic acid (11-octadecenoic acid), conjugate linoleic acid (9Z,11E-octadecadiene acid, 10Z,12E-octadecadiene acid, 10E,12Z-octadecadiene acid, 10Z,12Z-octadecadiene acid), dihomo-γ-linolenic acid ((8Z,11Z,14Z)-icosa-8,11,14-trienoic acid), α-linolenic acid ((9Z,12Z,15Z)-9,12,15-octadecatrienoic acid), γ-linolenic acid ((6Z,9Z,12Z)-6,9,12-octadecatrienoic acid), eleostearic acid ((9E,11E,13E)-9,11,13-octadecatrienoic acid), stearidonic acid ((6Z,9Z,12Z,15Z)-octadeca-6,9,12,15-tetraenoic acid), arachidonic acid ((5Z,8Z,11Z,14Z)-icosa-5,8,11,14-tetraenoic acid), eicosapentaenoic acid ((5Z,8Z,11Z,14Z,17Z)-icosa-5,8,11,14,17-pentaenoic acid), docosahexaenoic acid ((4Z,7Z,10Z,13Z,16Z,19Z)-docosa-4,7,10,13,16,19-hexaenoic acid), (n-6) docosapentaenoic acid ((4Z,7Z,10Z,13Z,16Z)-4,7,10,13,16-docosapentaenoic acid), and (n-3)docosapentaenoic acid ((7Z,10Z,13Z,16Z,19Z)-7,10,13,16,19-docosapentaenoic acid).

Among the unsaturated fatty acid listed above, docosahexaenoic acid, eicosapentaenoic acid, arachidonic acid, α-linolenic acid, γ-linolenic acid, linoleic acid, and oleic acid are preferred in view of the effect and convenience and linoleic acid is more preferred.

A saturated fatty acids from which the aforementioned acyl group is derived may be any of linear or branched saturated fatty acid not limited in the number of carbon atoms, but it is preferably a saturated fatty acid having 5 to 22 carbon atoms. Specific examples include linear saturated fatty acids such as caproic acid, caprylic acid, capric acid, lauric acid, myristic acid, palmitic acid, stearic acid, arachidic acid, and docosanoic acid; and branched saturated fatty acids such as 2-ethylhexanoic acid, 3,5,5-trimethylhexanoic acid, isotridecanoic acid, 2-hexyldecanoic acid, 2-hexyldodecanoic acid, 2-octyldecanoic acid, isostearic acid, and 2-octyldodecanoic acid.

Fatty acid glycerides to be used in the present invention may be any of monoglycerides, diglycerides, and triglycerides, but diglycerides are preferred, 1,3-diglycerides having unsaturated fatty acids described above attached to the first and third positions of glycerin are more preferred, and 1,3-diglycerides having linoleic acid attached to the third position are further preferred. When they are diglycerides or triglycerides, unsaturated fatty acids attached to the first, second, or third position of glycerin may be the same or different.

The fatty acid glycerides to be used in the present invention may be one fatty acid glyceride, but they are preferably a mixtures of two or more fatty acid glycerides. Use of two or more fatty acid glycerides together enhances the undifferentiated state-maintaining effect on stem cells, the proliferation-promoting effect on stem cells, or the wound healing effect. When two or more fatty acid glycerides are used together, the combination thereof is not particularly limited and may be any of monoglyceride and diglyceride, monoglyceride and triglyceride, diglyceride and triglyceride, and monoglyceride and diglyceride and triglyceride. Moreover, when two or more fatty acid glycerides are used together, the ratio thereof is not particularly limited and may vary as appropriate depending on the type of the fatty acid glycerides, but an example is from 10:90 to 90:10 when two types of diglyceride are used together. Besides the fatty acid glycerides according to the present invention, fatty acid glycerides not according to the present invention may be used together.

The fatty acid glycerides to be used in the present invention can be obtained by a method involving pressing, extracting, or pressing and extracting from plant or animal materials, an enzymatic method, or an organic synthetic method. Moreover, monoglycerides and diglycerides, among the aforementioned fatty acid glycerides, are generally used as emulsifiers, thickening stabilizers, and plasticizers in the production of foods, cosmetic products, pharmaceutical products, industrial chemicals, and the like. Triglycerides are main ingredients of vegetable oils and fats such as palm oil, cacao butter, coconut oil, and palm kernel oil and animal oils and fats such as milk fat, beef fat, lard, fish oil, and whale oil and widely used in cosmetic products and foods mainly. Therefore, the fatty acid glycerides to be used in the present invention may be commercially available products generally used in the field of production described above.

When the fatty acid glycerides are extracted from, for example, plant materials (seeds, fruits, bark, etc. of plants), the method of extraction is not particularly limited, and may be a heating extraction or normal or low temperature extraction.

Examples of solvents to be used in extraction include water, lower alcohols (methanol, ethanol, 1-propanol, 2-propanol, 1-butanol, 2-butanol, and the like), liquid polyvalent alcohols (1,3-butylene glycol, propylene glycol, glycerin, and the like), ketones (acetone, methylethylketone; and the like), acetonitrile, esters (ethyl acetate, butyl acetate, and the like), hydrocarbons (hexane, heptane, liquid paraffin, and the like), and ethers (ethyl ether, tetrahydrofuran, propyl ether, and the like). One solvent or a mixture of two or more solvents among these solvents may be used. Preferably, a mixture of water and a lower alcohol (hydrous lower alcohol) may be used, particularly preferably a mixture of water and ethanol (hydrous ethanol) may be used, and for example an aqueous solution of 50 to 90 v/v % ethanol may be used.

Moreover, the aforementioned extraction solvents whose pH is adjusted by adding acid or alkali may be used.

Examples of the percentage of plant materials to the extraction solvents include 1 to 50% (w/w), and preferably 5 to 25% (w/w). For example, fatty acid glycerides can be obtained by adding an aforementioned solvent to a dried plant material and conducting extraction at 5 to 80° C. Alternatively, fatty acid glycerides can be obtained by adding a lower alcohol (for example, ethanol) or a liquid polyhydric alcohol (for example, propylene glycol, 1,3-butylene glycol) is added to a dried plant material and conducting extraction at normal temperature (for example, 5 to 35° C.).

After the extraction with a solvent, the obtained solvent phase itself can be used as a fatty acid glyceride solution. Alternatively, the obtained solvent phase may be subjected, as needed, to a treatment such as concentration (concentration by concentration under reduced pressure, membrane concentration, or the like), dilution, filtration, or drying, or a decoloration or deodorization treatment by active carbon, or the like to prepare a fatty acid glyceride solution from the obtained product. Also, prior to use, purification is preferably conducted by an established purification method such as chromatography, distillation under reduced pressure, and crystallization. Furthermore, the extracted solution may be subjected to concentration and drying, or the extracted solution together with excipients may be subjected to a treatment such as concentration and drying, spray drying, and freeze-drying, and the resultant dry preparation can be used as fatty acid glycerides.

When fatty acid glycerides are extracted from animal materials (for example, parts of fish such as sardine and tuna), the fatty acid glycerides can be obtained by pressing the animal material, centrifuging an oil fraction to harvest oil, and extracting fat content with an organic solvent such as ethyl alcohol, hexane, ethyl acetate, or a mixed solvent thereof. After the extraction with a solvent, purification by chromatography or the like may be conducted in a method similar to that for plant materials.

The structure of fatty acid glycerides obtained from plant or animal materials can be confirmed by determining the structure of the side chains of the fatty acids identified by hydrolysis and the binding positions can be confirmed by nuclear magnetic resonance analysis.

A representative example of the enzymatic method is a method using lipase and other examples include methods involving hydrolysis of oils and fats, esterification of a fatty acid derived from oils and fats and glycerin, and transesterification between oils and fats and glycerin (intermolecular reaction, intramolecular reaction, acidolysis, alcoholysis). The oils and fats may be any of plant oils and fats (rapeseed oil, sesame oil, soybean oil, corn oil, sunflower oil, palm oil, palm karnel oil, coconut oil, safflower oil, linseed oil, cotton seed cake oil, castor oil, coconut oil, ad the like), animal oils and fats (beef fat, swine oil, fish oil), used oils of various edible oils (waste cooking oils), and the like.

The organic synthetic method can achieve reactions similar to those described above using chemical catalysts instead of enzymes. Example of chemical catalysts that can be used include alkali catalysts (sodium hydroxide, potassium hydroxide, sodium carbonate, potassium carbonate, and the like), acid catalysts (sulfuric acid, sulfonic acid, phosphoric acid, and the like), solid acid catalysts (composite metal compounds, metal sulfates, heteropolyacids, synthetic zeolite, ion-exchange resins, and the like). Furthermore, fatty acid glycerides can be prepared by methods involving reacting fatty acid chloride with glycerin, monoglyceride, or diglyceride, which is a usual method in organic synthesis. These fatty acid glycerides may be also subjected to purification described above.

The fatty acid glycerides obtained in such a way have a function of having stem cells efficiently proliferate while maintaining the undifferentiated state at a living body level or a culture level without the progression of differentiation during the proliferation of stem cells and can be used as an agent for maintaining the undifferentiated state or promoting the proliferation of stem cells. Furthermore, the agents for maintaining the undifferentiated state or promoting the proliferation of stem cells according to the present invention can be also used as an additive for cell culture to effectively proliferate stem cells while maintaining the undifferentiated state or a reagent for study.

The agents for maintaining the undifferentiated state or promoting the proliferation of stem cells according to the present invention can be applied to stem cells in mammals including humans to maintain the undifferentiated state of the stem cell and to promote proliferation of the stem cells. Stem cells to which the agents for maintaining the undifferentiated state or promoting the proliferation of stem cells according to the present invention are applied are not particularly limited as long as they meet the purpose of the present invention and examples thereof include embryonic stem cells (ES cells); somatic stem cells that reside in bone marrow, blood, skin (epidermis, dermis, subcutaneous tissue), fat, hair follicle, brain, nerve, liver, pancreas, kidney, muscle and other tissues; and stem cells produced artificially by genetic introduction (induced pluripotent stem cells: iPS cells). Preferably, agents for maintaining the undifferentiated state or promoting the proliferation of stem cells according to the present invention are more effective for stem cells derived from bone marrow, blood, skin, or adipose tissue. Examples of the ES cells include ES cells established by culturing an early embryo before the implantation, ES cells established by culturing an early embryo produced by nuclear transplantation of a somatic nucleus, and ES cells obtained by modifying a gene on a chromosome in these ES cells using a technique in genetic engineering. For example, such ES cells can be produced by a method known per se, can be obtained from certain organizations, and can be purchased as a marketed product. Moreover, these stem cells may be any of primary culture cells, successively cultured cells, or frozen cells.

Furthermore, the agents for maintaining the undifferentiated state or promoting the proliferation of stem cells according to the present invention can be applied to stem cells derived from all mammals if the stem cells have an equivalent property as to the direction of differentiation of the stem cells and the process of differentiation. The agents for maintaining the undifferentiated state or promoting the proliferation of stem cells according to the present invention may be effective for stem cells in mammals such as humans, monkeys, mice, rats, guinea pigs, rabbits, cats, dogs, horses, cows, sheep, goats, and pigs.

The agents for maintaining the undifferentiated state or promoting the proliferation of stem cells according to the present invention can be applied to stem cells in vitro or in vivo and they can be effective in either way. Therefore, the agents for maintaining the undifferentiated state or promoting the proliferation of stem cells according to the present invention can be added at an effective amount to a medium for stem cell culture to culture stem cells in the medium or administered to mammals including humans to maintain the undifferentiated state and promote the proliferation of stem cells.

The agents for maintaining the undifferentiated state or promoting the proliferation of stem cells according to the present invention act on stem cells in tissues and organs in the living body, such as skin, osteoblast, cartilage, muscle, nerve, fat, and liver and are effective in treating, ameliorating, and preventing disorders and damages in the relevant tissues and organs, since the fatty acid glycerides contained in these agents as an active ingredient have excellent undifferentiated state-maintaining and proliferation-promoting effects on stem cells. Moreover, the agents for maintaining the undifferentiated state or promoting the proliferation of stem cells according to the present invention are effective in treating, ameliorating, and preventing diseases related to decrease or functional decline of stem cells in the aforementioned tissues and organs in the living body since stem cells exhibit decrease or functional decline with aging. Examples of the disorders or damages in tissues or organs and diseases related to decrease or functional decline of stem cells, in terms of examples related to skin, include wrinkle, slackness, spot, dullness, skin roughness, skin thickening, opened pores, acne scar, wound, scar, and keloid as well as damages of the scalp and hairs such as thinning hair and hair loss. Examples related to the bone include osteoporosis, bone fractures (vertebral compression fracture, femoral neck fracture), and the like; examples of the cartilage disease include osteoarthritis, rheumatoid arthritis, disc herniation, and the like; examples related to the nerve include spinal cord injury, facial paralysis, Alzheimer's disease, amyotrophic lateral sclerosis, Parkinson's disease, age-related memory impairment, and the like; examples related to blood include aplastic anemia, leukemia, and the like; examples related to cardiovascular disease include myocardial infarction, arteriosclerosis obliterans, and the like; examples related to dentistry include periodontal disease, alveolar bone damage due to pyorrhea, and the like; examples related to ophthalmology include retinitis pigmentosa, age-related macular degeneration, glaucoma and the like; examples related to liver, or pancreatic include hepatitis, liver cirrhosis, diabetes and the like; but are not limited to these.

The aforementioned fatty acid glycerides can be also used as an agent for treating a wound, since they have an excellent wound healing promotion effect. In particular, they are effective in curing skin wound, which is a damage of the epidermis or the dermis of the skin. The skin wound is not particularly limited in the severity or the depth. Examples include common wounds, such as cut wounds, laceration, chop wounds, abrasions, crush injuries, contusions, stab wounds, and bite wounds as well as decubitus ulcer, scald, burn, diabetic ulcer, leg ulcer/leg aneurysm, and the like.

The content of the fatty acid glycerides in an agent for maintaining the undifferentiated state or promoting the proliferation of stem cells or for treating a wound according to the present invention is not particularly limited. For example, it is preferably 0.00001 to 10% by weight and more preferably 0.0001 to 1% by weight of the total amount of the agent in terms of dry mass. The effect may be insufficiently exhibited when the content is less than 0.00001% by weight.

When an agent for maintaining the undifferentiated state or promoting the proliferation of stem cells or for treating a wound according to the present invention is administered to the living body, it can be administered as it is or can be, with a suitable additive, comprised in various compositions such as cosmetic products, quasi drugs, pharmaceutical products, and foods and drinks and provided in a range not impairing the effect of the present invention. The pharmaceutical products according to the present invention shall include drugs to be used for animals or veterinarian medicine.

When an agent for maintaining the undifferentiated state or promoting the proliferation of stem cells or for treating a wound according to the present invention is comprised in a cosmetic product or a quasi drug, the dosage form may be any of an aqueous solution system, a solubilized system, an emulsified system, a powder system, a powder dispersed system, an oil system, a gel system, an ointment system, an aerosol system, a water-oil two phase system, or a water-oil-powder three phase system. Moreover, the cosmetic products and quasi drugs may be prepared according to a known technique in the field by mixing an agent for maintaining the undifferentiated state or promoting the proliferation of stem cells or for treating a wound with a variety of components, additives, bases, and the like, selected depending on the type thereof, which are usually used in compositions for external application to skin, as appropriate. The cosmetic products and quasi drugs may be in the form of any of a liquid, an emulsion, a cream, a gel, a paste, a spray, and the like. Examples of the components comprised in the compositions for internal application to skin include oils and fats (olive oil, coconut oil, evening primrose oil, jojoba oil, castor oil, hydrogenated castor oil, and the like), waxes (lanoline, beeswax, carnauba wax, and the like), hydrocarbons (liquid paraffin, squalene, squalane, Vaseline, and the like), fatty acids (lauric acid, myristic acid, palmitic acid, stearic acid, behenic acid, and the like), higher alcohols (myristyl alcohol, cetanol, cetostearyl alcohol, stearyl alcohol, behenyl alcohol, and the like), esters (isopropyl myristate, isopropyl palmitate, cetyl octanoate, glycerin trioctanoate, octyldodecyl myristate, octyl stearate, stearyl stearate, and the like), organic acids (citric acid, lactic acid, α-hydroxyacetic acid, pyrrolidone carboxylic acid, and the like), saccharides (maltitol, sorbitol, xylobiose, N-acetyl-D-glucosamine, and the like), proteins and hydrolysates of proteins, amino acids and salt thereof, vitamins, plant and animal extracts, a variety of surfactants, humectants, ultraviolet absorbers, antioxidants, stabilizers, preservatives, biocides, fragrances, and the like.

Examples of types of the cosmetic products and the quasi drugs include lotion, emulsion, gel, serum, common cream, sunscreen, pack, mask, face wash, toilet soap, foundation, face powder, bath salt, body lotion, body shampoo, hair shampoo, hair conditioner, hair restorer, and the like.

When an agent for maintaining the undifferentiated state or promoting the proliferation of stem cells or for treating a wound according to the present invention is comprised in a pharmaceutical product, various dosage forms of formulations suitable for applying to the affected part can be formulated by mixing it with a pharmacologically and pharmaceutically acceptable additive. As the pharmacologically and pharmaceutically acceptable additive, a base or carrier for the formulation selected as appropriate, a filler, a diluent, a binder, a lubricant, a coating agent, a disintegrator or a disintegrating agent, a stabilizer, a preservative, an antiseptic, a bulking agent, a dispersant, a wetting agent, a buffer, a solvent or a solubilizing agent, a tonicity adjusting agent, a pH modifier, a propellant, a colorant, a sweetening agent, a corrigent, or a flavor may be added depending on the dosage form and application, as appropriate and various dosage forms that can be administered orally or parenterally, systemically or topically may be prepared by various known methods. When pharmaceutical products of the present invention are to be provided in aforementioned forms, they can be prepared by methods of production usually used by those skilled in the art, for example, methods for preparation illustrated in [2] Monographs for Preparations in General Rules for Preparations in the Japanese pharmacopeia.

The forms of the pharmaceutical products according to the present invention are not limited, but examples include oral preparations such as a tablet, a sugarcoating tablet, a capsule, a lozenge, a granular agent, a powdery agent, a solution, a pill, an emulsion, a syrup, a suspension, an elixir, an injection (for example, a subcutaneous injection, an intravenous injection, an intramuscular injection, an intraperitoneal injection), parenteral preparations such as an infusion, a suppository, an ointment, a lotion, an instillation, an air spray, a transdermal absorbent, a transmucosal absorbent, and an adhesive preparation. Moreover, they may be formulated into dry products to be re-dissolved before use; and injectable preparations are provided in a state of unit dose ampoules or multi-dose containers.

When an agent for maintaining the undifferentiated state or promoting the proliferation of stem cells or an agent for treating a wound is used as a pharmaceutical product for treating, ameliorating, and preventing the aforementioned skin-related damages and diseases, suitable forms of the pharmaceutical product are preparations for external use and examples include an ointment, a cream, a gel, a solution, an adhesive preparation (a cataplasm, a plaster), a foam, a spray, and a nebula. The ointment refers to a homogeneous semisolid preparation for external use and includes oleaginous ointments, emulsion ointments, and water-soluble ointments. The gel refers to a preparation for external use in which a hydrate compound of a water-insoluble component is suspended into an aqueous liquid. The solution refers to a liquid preparation for external use and includes a lotion, a suspension, an emulsion, and a liniment. When used as an agent for treating a wound of the skin, an ointment, a cream, a solution, and a spray are more preferred in view of the skin wound healing effect and easiness of use.

The pharmaceutical product according to the present invention functions as a prophylactic agent that prevent the development of the aforementioned diseases and/or a therapeutic agent that restores the normal state. The active ingredients of the pharmaceutical product according to the present invention are naturally occurring products and therefore very safe with no side effects. Accordingly, the pharmaceutical product can be administered orally or parenterally in a wide range of doses, when used as medicine for treating, ameliorating, and preventing the aforementioned diseases in mammals such as humans, mouse, rat, rabbit, dog, and cat.

The content of an agent for maintaining the undifferentiated state or prompting proliferation of stem cells or for treating a wound in a cosmetic product, a pharmaceutical product, or a quasi drug according to the present invention is not particularly limited, but preferably 0.001 to 30% by weight, and more preferably 0.01 to 10% by weight of the total weight of the formulation (composition) in terms of the dry solid content of fatty acid glycerides. The effect is low when the content is less than 0.001% by weight and no large enhancement of the effect is hardly found when the content is more than 30% by weight. The amounts described above are merely an illustration and may be set/adjusted as appropriate in consideration of the type and the form, generally used amounts, and efficacies and effects of the composition. In order to add an active ingredient in the formulation, the ingredient may be added before the formulation or during the production, which may be selected as appropriate in consideration of workability.

The agents for maintaining the undifferentiated state or promoting the proliferation of stem cells or for treating a wound according to the present invention may be comprised in foods and drinks. The foods and drinks in the present invention are meant to include, besides general foods and drinks, foods that can be taken in for the purpose of maintaining and increasing the health, not pharmaceutical products, for example, health foods, functional foods, functional health foods, or food for special dietary uses. The health foods include foods provided in the names of nutritional supplements, health supplements, and dietary supplements. The functional health foods are defined in Food Sanitation Act or Health Promotion Act and include foods for specified health uses and nutritional functional foods that can indicate specific effects on health, functions of nutritional components, and reduction of disease risks.

The forms of foods and drinks may be any form suitable for edible use, including, for example, solid, liquid, granule, powder, capsule, cream, or paste form. In particular, preferable forms of the aforementioned health foods include forms of tablet, pill, capsule, powder, granule, fine granule, troche, and liquid (including syrup, emulsion, suspension).

Types of foods and drinks include, but are not limited to, bread, noodles, confectionery, dairy products, processed foods of fisheries and live stock products, oils and fats and oils and fats processed foods, seasoning, various drinks (refreshing drinks, carbonated drinks, beauty drinks, nutrition drinks, fruit drinks, milk drinks), and concentrated stock solutions and powder for adjustment of the drinks, and the like.

Additives that are usually used depending on the types may be added to the drinks and foods of the present invention as appropriate. Any additive that can be permitted under Food Sanitation Act may be used as the additive, but examples include sweeteners such as glucose, sucrose, fructose, isomerized sugar syrup, aspartame, stevia, and the like; acidulants such as citric acid, malic acid, tartaric acid, and the like; fillers such as dextrin, starch, a binder, a diluent, a flavor, a coloring agent, a buffer, a thickener, a gelling agent, a stabilizer, a preservative, an emulsifier, a dispersant, a suspending agent, an antiseptic, and the like.

When the foods and drinks of the present invention are general foods and drinks, the foods and drinks of the present invention can be produced by including the step of adding the fatty acid glycerides in the usual production process of the foods and drinks. Moreover, when the foods and drinks of the present invention are health foods, they can be produced according to the production process of the aforementioned pharmaceutical products: for example, supplement tablets can be produced by adding additives such as fillers to the fatty acid glycerides, mixing and tableting with pressure with a tableting machine or the like. Moreover, other materials (for example, vitamins such as vitamin C, vitamin $B_2$, vitamin $B_6$, minerals such as calcium, dietary fibers, and the like) can be added as needed.

The mixed amount of the fatty acid glycerides in the drinks and foods according to the present invention should be the amount at which the fatty acid glycerides can exhibit an undifferentiated state-maintaining effect and proliferation-promoting effect on stem cells and wound healing effect and should be set in consideration of the general intake of the drinks and foods, the shapes of the drinks and foods, efficacies and effects, tastes, preferences, and cost as appropriate.

The present invention also relates to a method for promoting the proliferation of stem cells while maintaining the undifferentiated state of the stem cells by culturing stem cells in a medium containing fatty acid glycerides. In other words, the method according to the present invention is considered to be a method for producing stem cells, a method for maintaining the undifferentiated state of stem cells, or a method for promoting the proliferation of stem cells, including the step of culturing stem cells in a medium containing fatty acid glycerides.

In the methods according to the present invention, media that are generally used for the maintenance of an undifferentiated state and proliferation of stem cells may be used for culturing the stem cells. Examples include basal media containing the components (inorganic salts, carbohydrates, hormones, essential amino acids, non-essential amino acids, vitamins, fatty acids) necessary for the survival and proliferation of the stem cells. Specific examples include Dulbecco's Modified Eagle Medium (D-MEM), Minimum Essential Medium (MEM), RPMI 1640, Basal Medium Eagle (BME), Dulbecco's Modified Eagle Medium Nutrient Mixture F-12 (D-MEM/F-12), Glasgow Minimum Essential Medium (Glasgow MEM), Hanks' solution (Hank's balanced salt solution), and the like. Moreover, basic fibroblast growth factor (bFGF) and/or leukocyte migration inhibition factor (LIF) may be added to the media as a growth factor. Furthermore, the media may contain, as need, epidermal growth factor (EGF), tumor necrosis factor (TNF), Vitamins, interleukins, insulin, transferrin, heparin, heparan sulfate, collagen, fibronectin, progesterone, Celenite, B27-supplement, N2-supplement, ITS-supplement, antibiotics, and the like.

Moreover, besides the aforementioned components, it is preferred that serum is contained in the media at a content of 1 to 20%. However, it is preferred to use serum after a lot check because serum has different components depending on the lot and the effect of serum is uneven.

The following commercially available media are available: Mesenchymal stem cell basal medium manufactured by Invitrogen, Mesenchymal stem cell basal medium manufactured by Sanko Junyaku Co., Ltd., MF medium manufactured by Toyobo Co., Ltd., and Hanks' solution (Hank's balanced salt solution) manufactured by Sigma.

Incubators to be used for culturing stem cells are not particularly limited as long as the stem cells can be cultured and examples include flasks, culture dishes, dishes, plates, chamber-slides, tubes, trays, culture bags, roller bottles, and the like.

The incubators may be non-adhesive to cells or may be adhesive to cells, which is selected as appropriate depending on the purpose. The incubators that are adhesive to cells may be those treated with a substrate for supporting cells made of an extracellular matrix for improving the adhesiveness with cells. Examples of the substrate for supporting cells include collagen, gelatin, poly-L-lysine, poly-D-lysine, laminin, fibronectin, and the like.

The concentrations of the fatty acid glycerides in the medium used for culturing stem cells may be determined, as appropriate, according to the aforementioned content of the fatty acid glycerides in the agent for maintaining the undifferentiated state or promoting the proliferation of stem cells according to the present invention and examples include concentrations of 0.1 to 1000 μg/mL, preferably 1 to 100 μg/mL. Moreover, the fatty acid glycerides may be added regularly to the medium during the culture period of the stem cells.

The culture conditions of the stem cells should be usual conditions used for culturing stem cells and no special control is required. The culture temperature is, for example, not particularly limited but it is approximately 30 to 40° C., and preferably 36 to 37° C. The $CO_2$ gas concentration is, for example, approximately 1 to 10%, and preferably approximately 2 to 5%. The medium change is preferably conducted once in 2 to 3 days and more preferably conducted every day. The above culture conditions may be changed and set as appropriate within the range that allows survival and proliferation of stem cells.

The maintenance of an undifferentiated state of stem cells may be evaluated, for example, by comparing the expression level of stem cells undifferentiation marker gene in stem cells cultured in the presence of an agent for maintaining the undifferentiated state of stem cells according to the present invention with the expression level in the same stem cells cultured in the absence of the agent for maintaining the undifferentiated state of stem cells according to the present invention; and determining whether the expression level of stem cells undifferentiation marker gene is significantly maintained at the same level as the expression level at the onset of culture at the mRNA or protein level. An example of the stem cell undifferentiation marker gene is the Nanog gene (Cell Res. 2007 January; 17 (1): 42-9. Review. Nanog and transcriptional networks in embryonic stem cell pluripotency. Pan G, Thomson J A.).

Examples of methods for measuring the stem cell undifferentiation marker gene expression level at the mRNA level include methods such as RT-PCR using primers or a probe that are specific for the stem cell undifferentiation marker gene, quantitative PCR, and Northern blotting. Examples at the protein level include immunological methods such as ELISA, flow cytometry, and Western blotting using an antibody that is specific for a protein encoded by the stem cell undifferentiation marker gene.

As a result of the measurement of the expression level, if the relative ratio of the expression level of the stem cell undifferentiation marker gene level in the stem cells after culturing for a predetermined time period in the presence of an agent for maintaining the undifferentiated state of stem cells of the present invention to the expression level of the stem cell undifferentiation marker gene in the stem cells at the onset of culture (100% undifferentiated state) is greater than the relative ratio (control) obtained by culturing the stem cells in the absence of the agent for maintaining the undifferentiated state of stem cells of the present invention, then it can be determined that the undifferentiated state of the stem cells was maintained.

Also, the promotion ofproliferation of stem cells can be evaluated by, for example, comparing the cell number of stem cells cultured in the presence of an agent for promoting the proliferation of stem cells according to the present invention with the number of stem cells cultured in the absence of the agent for promoting the proliferation of stem cells according to the present invention and determining whether the number of cells are significantly increased. The measurement of the cell number can be conducted using a commercially available cytometry kit for the MTT method or the WST method, for example. As a result of measurement, if the relative ratio of the cell number of the stem cells after culturing for a predetermined time period in the presence of the agent for promoting the proliferation of stem cells according to the present invention to the cell number of the stem cells at the onset of culture is greater than the relative ratio (control) obtained by culturing the stem cells in the absence of the agent for promoting the proliferation of stem cells according to the present invention, then it can be determined that the proliferation of the stem cells was promoted.

The stem cells prepared by the method according to the present invention described above can be used as transplant materials (cell transplant agents) and can be transplanted by the methods same as those for the conventional bone marrow or umbilical cord blood transplantation.

According to the agents for maintaining the undifferentiated state or promoting the proliferation of stem cells according to the present invention or the methods according to the present invention described above, fatty acid glycerides, alone or separately with a medium or mixed with a medium, can be provided as a reagent kit for maintaining the undifferentiated state or promoting the proliferation of stem cells. The kit may include an instruction manual or the like as needed. Alternatively, the fatty acid glycerides can be mixed with a medium and provided as a medium for maintaining the undifferentiated state or promoting the proliferation of stem cells

EXAMPLES

The present invention is described below with Examples in greater detail. The technical scope of the present invention is however not limited to these Examples.

Fatty acid glycerides used in the evaluation tests in Examples and their structures are illustrated in Table 1. As fatty acid glycerides 1 to 9, tripalmitin and palmitic acid of Comparative Examples, the following commercially available products or products synthesized by a method illustrated in Production Example or a similar method were used.

Fatty acid glycerides 1: Wako Pure Chemical Industries, Ltd.
Fatty acid glycerides 2: INDOFINE Chemical Company, Inc.
Fatty acid glycerides 3: NU-CHEK-PREP
Fatty acid glycerides 5: NU-CHEK-PREP
Fatty acid glycerides 6: MP Biomedicals
Fatty acid glycerides 8: Sigma-Aldrich Co. LLC
Fatty acid glycerides 9: Funakoshi Co., Ltd.
Fatty acid glycerides 4, 7: Synthesized by Production Example described below.
Tripalmitin: Wako Pure Chemical Industries, Ltd.
Palmitic acid: Wako Pure Chemical Industries, Ltd.

(Production Example) Synthesis of Diglycerides

Linoleic acid chloride was added to an ice cooled mixture of 1-monoolein and pyridine and the mixture was stirred at 0° C. for 24 hours. After the reaction, diethyl ether was added, pyridine was removed with 0.5 N hydrochloric acid, and extraction with a dilute aqueous solution of sodium carbonate was conducted. The ether solution was concentrated and dried to obtain crude diglyceride. This was purified by the silica gel column chromatography under usual conditions to obtain fatty acid glyceride 4. Fatty acid glyceride 7 was obtained by a method similar to that described above except that 2-monolinolein was used instead of 1-monoolein and palmitic acid chloride was used instead of linoleic acid chloride.

TABLE 1

| Fatty acid glyceride | Name | Structure |
|---|---|---|
| 1 | 1-Monoolinolein | $CH_2OH$<br>$\|$<br>$CHOH$<br>$\|$<br>$CH_2OCO(CH_2)_7CH=CHCH_2CH=CH(CH_2)_4CH_3$ |
| 2 | 1-Palmitin-3-linolein | $CH_2OCO(CH_2)_{14}CH_3$<br>$\|$<br>$CHOH$<br>$\|$<br>$CH_2OCO(CH_2)_7CH=CHCH_2CH=CH(CH_2)_4CH_3$ |
| 3 | 1,3-Dilinolein | $CH_2OCO(CH_2)_7CH=CHCH_2CH=CH(CH_2)_4CH_3$<br>$\|$<br>$CHOH$<br>$\|$<br>$CH_2OCO(CH_2)_7CH=CHCH_2CH=CH(CH_2)_4CH_3$ |
| 4 | 1-Olein-3-linolein | $CH_2OCO(CH_2)_7CH=CH(CH_2)_7CH_3$<br>$\|$<br>$CHOH$<br>$\|$<br>$CH_2OCO(CH_2)_7CH=CHCH_2CH=CH(CH_2)_4CH_3$ |
| 5 | 1-Stearin-3-linolein | $CH_2OCO(CH_2)_{16}CH_3$<br>$\|$<br>$CHOH$<br>$\|$<br>$CH_2OCO(CH_2)_7CH=CHCH_2CH=CH(CH_2)_4CH_3$ |
| 6 | 1,3-Diolein | $CH_2OCO(CH_2)_7CH=CH(CH_2)_7CH_3$<br>$\|$<br>$CHOH$<br>$\|$<br>$CH_2OCO(CH_2)_7CH=CH(CH_2)_7CH_3$ |

TABLE 1-continued

| Fatty acid glyceride | Name | Structure |
|---|---|---|
| 7 | 1-Palmitin-2-linolein | CH$_2$OCO(CH$_2$)$_{14}$CH$_3$<br>\|<br>CHOCO(CH$_2$)$_7$CH=CHCH$_2$CH=CH(CH$_2$)$_4$CH$_3$<br>\|<br>CH$_2$OH |
| 8 | Triolein | CH$_2$OCO(CH$_2$)$_7$CH=CH(CH$_2$)$_7$CH$_3$<br>\|<br>CHOCO(CH$_2$)$_7$CH=CH(CH$_2$)$_7$CH$_3$<br>\|<br>CH$_2$OCO(CH$_2$)$_7$CH=CH(CH$_2$)$_7$CH$_3$ |
| 9 | Trilinolein | CH$_2$OCO(CH$_2$)$_7$CH=CHCH$_2$CH=CH(CH$_2$)$_4$CH$_3$<br>\|<br>CHOCO(CH$_2$)$_7$CH=CHCH$_2$CH=CH(CH$_2$)$_4$CH$_3$<br>\|<br>CH$_2$OCO(CH$_2$)$_7$CH=CHCH$_2$CH=CH(CH$_2$)$_4$CH$_3$ |

Example 1

Evaluation of Undifferentiated State-Maintaining Effect and Proliferation-Promoting Effect of Fatty Acid Glycerides on Stem Cells Experimental Examples and results thereof on the undifferentiated state-maintaining effect and the proliferation-promoting effect on stem cells using one or a mixture (fatty acid glycerides 2+3, fatty acid glycerides 4+5) of fatty acid glycerides 1 to 9 are described below. When a mixture of two fatty acid glycerides was used, the ratio thereof was 1:1 (weight ratio).

(Experimental Example 1) Evaluation of Undifferentiated State-Maintaining Effect on Stem Cells Using a medium prepared by adding fetal bovine serum (FBS, 15%, manufactured by Sigma-Aldrich Co. LLC), a nucleoside solution (100 times dilution, manufactured by Sumitomo Dainippon Pharma Co., Ltd.), a non-essential amino acids solution (100 times dilution, manufactured by Sumitomo Dainippon Pharma Co., Ltd.), a β2-mercaptoethanol solution (100 times dilution, manufactured by Sumitomo Dainippon Pharma Co., Ltd.), an L-glutamine solution (100 times dilution, manufactured by Sumitomo Dainippon Pharma Co., Ltd.), penicillin (100 units/mL, manufactured by Sigma-Aldrich Co. LLC), and streptomycin (100 µg/mL, manufactured by Sigma-Aldrich Co. LLC) to Dulbecco's Modified Eagle Medium (manufactured by Gibco), 5×10$^5$ cells of murine embryonic stem cells (murine ES cells: manufactured by COSMO BIO Co., Ltd.) were seeded in a 6 cm dish coated with gelatin (manufactured by Sigma-Aldrich Co. LLC), one or a mixture of fatty acid glycerides 1 to 9 was added to the medium at a final concentration of 0.001%, and culture was continued for 3 days.

After 3 days of culture, cells were collected and washed twice with PBS(−) and RNA was extracted from the cells with Trizol Reagent (Invitrogen). Extracted RNA was reverse-transcripted to cDNA using 2-STEP real-time PCR kit (Applied Biosystems) and then real-time PCR (95° C.: 15 seconds, 60° C.: 30 seconds, 40 cycles) was performed by AB17300 (Applied Biosystems) using the following primer sets to confirm the gene expression of Nanog (undifferentiation marker: Cell Res. 2007 January; 17 (1): 42-9. Review. Nanog and transcriptional networks in embryonic stem cell pluripotency. Pan G, Thomson J A.). Other operations were conducted according to a determined procedure.

```
Primer set for Nanog (undifferentiation marker):
                                        (SEQ ID NO: 1)
ATGCCTGCAGTTTTTCATCC (SEQ ID NO: 2)
GAGGCAGGTCTTCAGAGGAA Primer set for Gapdh (internal standard):
                                        (SEQ ID NO: 3)
TGCACCACCAACTGCTTAGC (SEQ ID NO: 4)
TCTTCTGGGTGGCAGTGATG
```

The undifferentiated state-maintaining effect was evaluated as follows: the value of the relative gene expression level of Nanog (Nanog gene expression level/Gapdh gene expression level) calculated as the ratio of the Nanog mRNA expression level to the Gapdh mRNA expression level, which is an internal standard, in murine ES cells at the onset of culture was defined as 100% undifferentiation; and relative thereto, the value of the relative gene expression level of Nanog in the ES cells after 3 days of culture was calculated and evaluated.

These test results are illustrated in Table 2 below.

TABLE 2

Evaluation of undifferentiated state-maintaining effect of fatty acid glycerides on stem cells

| Test substance | Nanog expression level (%) after 3 days of culturing |
|---|---|
| No addition (Control) | 25 |
| Fatty acid glyceride 1 | 33 |
| Fatty acid glyceride 2 | 71 |
| Fatty acid glyceride 3 | 65 |
| Fatty acid glyceride 4 | 59 |
| Fatty acid glyceride 5 | 57 |
| Fatty acid glyceride 6 | 43 |
| Fatty acid glyceride 7 | 41 |
| Fatty acid glyceride 8 | 35 |
| Fatty acid glyceride 9 | 34 |
| Fatty acid glyceride 2 + 3 | 83 |
| Fatty acid glyceride 4 + 5 | 77 |

TABLE 2-continued

Evaluation of undifferentiated state-maintaining effect of fatty acid glycerides on stem cells

| Test substance | Nanog expression level (%) after 3 days of culturing |
|---|---|
| Tripalmitin (Comparative Example 1) | 26 |
| Palmitic acid (Comparative Example 2) | 27 |

* Analyzed with the relative gene expression level of Nanog expressed in ES cells at the onset of culture defined as 100% undifferentiation.

As illustrated in Table 2, all of fatty acid glycerides 1 to 9 were found to have a significant undifferentiated state-maintaining effect on stem cells and the effect was enhanced by using two or more fatty acid glycerides together. Based on the foregoing, an excellent undifferentiated state-maintaining effect of fatty acid glycerides on stem cells was elucidated. Besides the stem cells used in this Experimental Example, significant undifferentiated state-maintaining effects on stem cells were found in somatic stem cells in similar tests.

(Experimental Example 2) Evaluation of Proliferation-Promoting Effect on Stem Cells $3 \times 10^5$ cells of human somatic stem cells (manufactured by DS Pharma Biomedical Co., Ltd.) cultured using a human stem cell culture medium (manufactured by Toyobo Co., Ltd.) were seeded in a 6 cm dish, one or a mixture (fatty acid glycerides 2+3, fatty acid glycerides 4+5) of fatty acid glycerides 1 to 9 was added at a final concentration of 0.001%, and culture was continued for 3 days. When a mixture of two fatty acid glycerides was used, the ratio thereof was 1:1 (weight ratio).

After 3 days of culture, cells were washed three times with PBS(−), then collected with a rubber policeman, and cells were counted for each culture.

The total number of cells without addition of fatty acid glycerides was defined as control and the control was defined as 100(%). Increase or decrease (%) of the number of cells with addition of fatty acid glycerides was calculated and the stem cell proliferation-promoting effect was evaluated.

These test results are illustrated in Table 3 below.

TABLE 3

Evaluation of proliferation-promoting effect of fatty acid glycerides on stem cells

| Test substance | Percent cell proliferation (%) |
|---|---|
| No addition (Control) | 100.0 |
| Fatty acid glyceride 1 | 115.1 |
| Fatty acid glyceride 2 | 160.3 |
| Fatty acid glyceride 3 | 157.8 |
| Fatty acid glyceride 4 | 148.3 |
| Fatty acid glyceride 5 | 145.3 |
| Fatty acid glyceride 6 | 130.1 |
| Fatty acid glyceride 7 | 129.3 |
| Fatty acid glyceride 8 | 118.3 |
| Fatty acid glyceride 9 | 117.3 |
| Fatty acid glyceride 2 + 3 | 180.6 |
| Fatty acid glyceride 4 + 5 | 178.3 |
| Tripalmitin (Comparative Example 1) | 103.2 |
| Palmitic acid (Comparative Example 2) | 102.1 |

* Shown is percent increase in the number of cells in each of the fatty acid glyceride addition groups relative to the number of cells in the no addition group (control) after 3 days of culturing defined as 100%.

As illustrated in Table 3, all of fatty acid glycerides 1 to 9 were found to have a significant proliferation-promoting effect on stem cells. Also, the effect was enhanced by using two or more fatty acid glycerides together. The number of human somatic stem cells in the onset of culture was 25% when the number of the aforementioned control was expressed as 100%. Based on the foregoing, an excellent stem cell proliferation-promoting effect of fatty acid glycerides was elucidated. Besides the stem cells used in this Experimental Example, significant stem cell proliferation-promoting effects were found in embryonic stem cells (ES cells) in similar tests.

Example 2

In Vitro Wound Healing Test (Scratch Assay)

The scratch assay (JP Publication (Kokai) No. 2013-18756), which is generally conducted as a method for evaluating the efficacy to promote wound healing, was conducted. Specifically, $5 \times 10^5$ cells of human somatic stem cells were seeded in a 3.5 cm dish, cultured using human stem cell culture medium to confluency, and then the bottom of the dish was scratched with the end of a sterilized tip to generate a gap in the cell sheet. Subsequently, the medium was changed to a medium supplemented with one or a mixture (fatty acid glycerides 2+3, fatty acid glycerides 4+5) of fatty acid glycerides 1 to 9 at a final concentration of 0.001% and the percent recovery of the cell gap was evaluated 48 hours later. To obtain the same area under a phase contrast microscope when obtaining images before and after the recovery, a mark that can be used as a reference point is provided near the scratch.

The scratch region 48 hours later was calculated as [scratch region 48 hours later]=100× [area of scratch region at 48 hours]/[area of scratch region at 0 hours] using a commercially available image analysis software. These test results are illustrated in Table 4 below.

TABLE 4

Evaluation of in vitro wound healing effect of fatty acid glycerides on stem cells

| Test substance | Scratch region 48 hours later (%) |
|---|---|
| No addition (Control) | 61 |
| Fatty acid glyceride 1 | 54 |
| Fatty acid glyceride 2 | 30 |
| Fatty acid glyceride 3 | 32 |
| Fatty acid glyceride 4 | 38 |
| Fatty acid glyceride 5 | 40 |
| Fatty acid glyceride 6 | 44 |
| Fatty acid glyceride 7 | 45 |
| Fatty acid glyceride 8 | 52 |
| Fatty acid glyceride 9 | 53 |
| Fatty acid glyceride 2 + 3 | 21 |
| Fatty acid glyceride 4 + 5 | 25 |
| Tripalmitin (Comparative Example 1) | 59 |
| Palmitic acid (Comparative Example 2) | 60 |

* [scratch region 48 hours later] = 100 × [area of scratch region at 48 hours]/[area of scratch region at 0 hours]

As illustrated in Table 4, a significant in vitro wound healing effect was found in all of the fatty acid glycerides. Also, the effect was enhanced by using two or more fatty acid glycerides together.

As illustrated in Experimental Examples above, it has become possible to promote proliferation of stem cells while maintaining the undifferentiated state easily and effectively in comparison with conventional techniques by applying fatty acid glycerides to the stem cells. The fatty acid glycerides according to the present invention also exhibited an excellent wound healing effect.

Example 3

Formulation Examples for Products

Formulation Examples for products containing one or a mixture of fatty acid glycerides 1 to 9 are illustrated below. In Formulation Examples below, "fatty acid glyceride" means one of fatty acid glycerides 1 to 9 or either of the equal amount mixture of fatty acid glycerides 2 and 3 and the equal amount mixture of fatty acid glycerides 4 and 5.

(Formulation Example 1) Lotion

| Formulation | Mixed amount (weight %) |
|---|---|
| 1. Fatty acid glyceride | 0.1 |
| 2. 1,3-butylene glycol | 8.0 |
| 3. Glycerin | 2.0 |
| 4. Xanthan gum | 0.02 |
| 5. Citric acid | 0.01 |
| 6. Sodium citrate | 0.1 |
| 7. Ethanol | 5.0 |
| 8. Methyl parahydroxybenzoate | 0.1 |
| 9. Polyoxyethylene hydrogenated castor oil (40 E.O.) | 0.1 |
| 10. Fragrance | 0.1 |
| 11. Purified water | balance |

A lotion is prepared by homogenously dissolving components 2 to 6 and 11 and components 1 and 7 to 10 separately, then mixing them, and filtering the mixture.

(Formulation Example 2) Cream

| Formulation | Mixed amount (weight %) |
|---|---|
| 1. Fatty acid glyceride | 0.1 |
| 2. Squalane | 5.5 |
| 3. Olive oil | 3.0 |
| 4. Stearic acid | 2.0 |
| 5. Beeswax | 2.0 |
| 6. Octyldodecyl myristate | 3.5 |
| 7. Polyoxyethylene cetyl ether (20 E.O.) | 3.0 |
| 8. Behenyl alcohol | 1.5 |
| 9. Glyceryl monostearate | 2.5 |
| 10. Fragrance | 0.1 |
| 11. Methyl parahydroxybenzoate | 0.2 |
| 12. Ethyl parahydroxybenzoate | 0.05 |
| 13. 1,3-butylene glycol | 8.5 |
| 14. Purified water | balance |

Components 1 to 9 are heated, dissolved, mixed and kept at 70° C. to form an oil phase. Components 11 to 14 are heated, dissolved, mixed, and kept at 75° C. to form a water phase. Then, the water phase is added to the oil phase and the mixture is emulsified and cooled with agitation. Component 10 is added at 45° C. and the mixture is further cooled to 30° C. to yield the product.

(Formulation Example 3) Emulsion

| Formulation | Mixed amount (weight %) |
|---|---|
| 1. Fatty acid glyceride | 0.1 |
| 2. Squalane | 5.0 |
| 3. Olive oil | 5.0 |
| 4. Jojoba oil | 5.0 |
| 5. Cetanol | 1.5 |
| 6. Glyceryl monostearate | 2.0 |
| 7. Polyoxyethylene cetyl ether (20 E.O.) | 3.0 |
| 8. Polyoxyethylene sorbitan monooleate (20 E.O.) | 2.0 |
| 9. Fragrance | 0.1 |
| 10. Propylene glycol | 1.0 |
| 11. Glycerin | 2.0 |
| 12. Methyl parahydroxybenzoate | 0.2 |
| 13. Purified water | balance |

Components 1 to 8 are heated, dissolved, mixed, and kept at 70° C. to form an oil phase. Components 10 to 13 are heated, dissolved, mixed, and kept at 75° C. to form a water phase.

The water phase is added to the oil phase and the mixture is emulsified and cooled with agitation. Component 9 is added at 45° C. and the mixture is further cooled to 30° C. to yield the product.

(Formulation Example 4) Gel

| Formulation | Mixed amount (weight %) |
|---|---|
| 1. Fatty acid glyceride | 0.1 |
| 2. Ethanol | 5.0 |
| 3. Methyl parahydroxybenzoate | 0.1 |
| 4. Polyoxyethylene hydrogenated castor oil | 0.1 |
| 5. Fragrance | q.s. |
| 6. 1,3-butylene glycol | 5.0 |
| 7. Glycerin | 5.0 |
| 8. Xanthan gum | 0.1 |
| 9. Carboxyvinyl polymer | 0.2 |
| 10. Potassium hydroxide | 0.2 |
| 11. Purified water | balance |

Components 1 to 5 and components 6 to 11 are each homogenously dissolved and both are mixed to yield the product.

(Formulation Example 5) Ointment

| Formulation | Mixed amount (weight %) |
|---|---|
| 1. Fatty acid glyceride | 2.0 |
| 2. Polyoxyethylene cetyl ether (30 E.O.) | 2.0 |
| 3. Glyceryl monostearate | 10.0 |
| 4. Liquid paraffin | 5.0 |
| 5. Cetanol | 6.0 |
| 6. Methyl parahydroxybenzoate | 0.1 |
| 7. Propylene glycol | 10.0 |
| 8. Purified water | balance |

Components 1 to 5 are heated, dissolved, mixed, and kept at 70° C. to form an oil phase. Components 6 to 8 are heated, dissolved, mixed, and kept at 75° C. to form a water phase.

The water phase is added to the oil phase and the mixture is emulsified, cooled to 30° C. with agitation to yield the product.

(Formulation Example 6) Pack

| Formulation | Mixed amount (weight %) |
|---|---|
| 1. Fatty acid glyceride | 0.1 |
| 2. Polyvinyl alcohol | 12.0 |
| 3. Ethanol | 5.0 |
| 4. 1,3-butylene glycol | 8.0 |
| 5. Methyl parahydroxybenzoate | 0.2 |
| 6. para-Oxyethylene hydrogenated castor oil (20 E.O.) | 0.5 |
| 7. Citric acid | 0.1 |
| 8. Sodium citrate | 0.3 |
| 9. Fragrance | q.s. |
| 10. Purified water | balance |

Components 1 to 10 are dissolved homogenously to yield the product.

(Formulation Example 7) Tablet

| Formulation | Mixed amount (weight %) |
|---|---|
| 1. Fatty acid glyceride | 1.0 |
| 2. Dry cornstarch | 25.0 |
| 3. Calcium carboxymethylcellulose | 20.0 |
| 4. Crystallite cellulose | 40.0 |
| 5. Polyvinylpyrrolidone | 8.0 |
| 6. Talc | 6.0 |

Components 1 to 5 are mixed, 10% of water is then added as a binder thereto, and the mixture is extruded, granulated, and then dried. Component 6 is added to and mixed with formed granules and compressed into tablets. A tablet shall be 0.52 g.

(Formulation Example 8) Drink

| Formulation | Mixed amount (weight %) |
|---|---|
| 1. Fatty acid glyceride | 0.1 |
| 2. Stevia | 0.05 |
| 3. Malic acid | 5.0 |
| 4. Flavor | 0.1 |
| 5. Purified water | balance |

Components 1 to 4 are dissolved in a part of component 5, purified water, with stirring. Then, the remaining purified water of component 5 is added and mixed. The solution is heated to 90° C. and filled into a 50 mL glass bottle.

INDUSTRIAL AVAILABILITY

Examples of expected application of the present invention include regenerative medicine and regenerative cosmetic treatments. For example, it becomes possible to easily and efficiently prepare stem cells in an undifferentiated state to be used for regenerative medicine or a regenerative cosmetic treatment by employing the present invention. Furthermore, the fatty acid glycerides according to the present invention can be injected directly or administered by oral administration, application, pasting, or the like after transplanting stem cells or to stem cells that reside in tissue to proliferate the stem cells while maintaining the undifferentiated state. Moreover, the fatty acid glycerides according to the present invention can be used as an excellent agent for treating a wound.

More specifically, the present invention is available as a method for preparing stem cells in regenerative medicine and regenerative cosmetic treatment and/or an agent for maintaining the undifferentiated state or promoting the proliferation of stem cells or an agent for treating a wound.

All publications, patents, and patent applications cited herein are incorporated herein by reference as they are.

The invention claimed is:

1. A method for promoting proliferation of stem cells, comprising culturing stem cells in a medium comprising fatty acid diglycerides comprising at least one of 1-Palmitin-3-linolein, 1,3-Dilinolein, 1-Olein-3-linolein, 1-Stearin-3-linolein, 1,3-Diolein, and 1-Palmitin-2-linolein.

2. The method according to claim 1, wherein said fatty acid diglycerides comprise at least 1-Palmitin-3-linolein.

3. A method for promoting proliferation of stem cells in a mammal, comprising administering to the mammal an effective amount of fatty acid diglycerides comprising at least one of 1-Palmitin-3-linolein, 1,3-Dilinolein, 1-Olein-3-linolein, 1-Stearin-3-linolein, 1,3-Diolein, and 1-Palmitin-2-linolein.

4. The method according to claim 3, wherein said fatty acid diglycerides comprise at least 1-Palmitin-3-linolein.

5. The method according to claim 1, wherein the fatty acid diglycerides comprises at least two of fatty acid diglycerides selected from the group consisting of 1-Palmitin-3-linolein, 1,3-Dilinolein, 1-Olein-3-linolein, 1-Stearin-3-linolein, 1,3-Diolein, and 1-Palmitin-2-linolein.

6. The method according to claim 3, wherein the fatty acid diglycerides comprises at least two of fatty acid diglycerides selected from the group consisting of 1-Palmitin-3-linolein, 1,3-Dilinolein, 1-Olein-3-linolein, 1-Stearin-3-linolein, 1,3-Diolein, and 1-Palmitin-2-linolein.

7. The method according to claim 1, wherein an effective amount for promoting proliferation of stem cells of a mixture of two or more of said fatty acid diglycerides is used.

8. The method according to claim 3 wherein an effective amount for promoting proliferation of stem cells of a mixture of two or more of said fatty acid diglycerides is used.

* * * * *